United States Patent

Sobotík et al.

[11] Patent Number: 5,504,208
[45] Date of Patent: Apr. 2, 1996

[54] PROCESS FOR THE PREPARATION OF 3, 14β-DIHYDROXY-17-NORMORPHINAN

[75] Inventors: Roman Sobotík; Petr Bulej, both of Opava; Tomáš Kolašín, Ostrava; Alexandr Jegorov, České Budějovice; Petr Sedmera, Prague; Aleš Husek; Anna Jurčáková, both of Opava, all of Czechoslovakia

[73] Assignee: Galena a.s., Komarov, Czech Rep.

[21] Appl. No.: 278,945

[22] Filed: Jul. 22, 1994

[30] Foreign Application Priority Data

Aug. 13, 1993 [CZ] Czech Rep. .............................. 1669-93

[51] Int. Cl.⁶ .................................................. C07D 221/28
[52] U.S. Cl. ............................................. 546/74; 514/289
[58] Field of Search ....................................... 546/74

[56] References Cited

U.S. PATENT DOCUMENTS 3,819,635  6/1974  Pachter et al. ............................ 546/74

FOREIGN PATENT DOCUMENTS 163-93  2/1993  Czechoslovakia .

OTHER PUBLICATIONS

Article–Ceskoslov, Fram. 32, 1983, No. 1, pp. 23–26.

*Primary Examiner*—Alan L. Rotman
*Attorney, Agent, or Firm*—Bachman & LaPointe

[57] ABSTRACT

Process for the preparation of 3,14β-dihydroxy-17-normorphinan

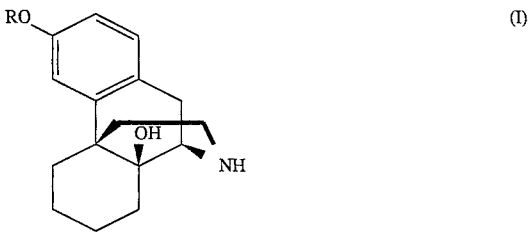

A suitable economic process for the preparation of 3,14β-dihydroxy-17-normorphinan of a general formula (I) is being solved, which is a key intermediate of a semisynthetic synthesis of an effective analgesic of Butorphanol from thebaine.

Synthesis includes a two step N-demethylation, and concerted dephenoxylation of 4-phenoxy-14β-hydroxy-3-methoxymorphinan in the first step by means of a chloroformate, then, in the second step, by means of sodium action in a liquid ammonia, and by means of the following O-demethylation under action of a complex of aluminium chloride - dialkylsulfide.

1 Claim, No Drawings

PROCESS FOR THE PREPARATION OF 3,14β-DIHYDROXY-17-NORMORPHINAN

BACKGROUND OF THE INVENTION

1. Field of the Invention

The invention refers to the process for the preparation of 3,14β-dihydroxy-17-normorphinan of this general formula (I):

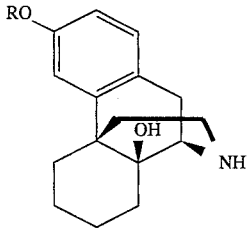

R=hydrogen.

This compound is a key intermediate within the synthesis of 3,14β-dihydroxy-17-cycloalkylmethylmorphinans of a general formula (II):

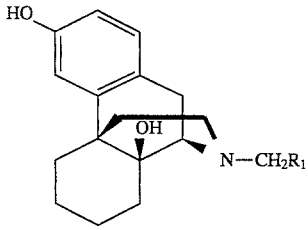

wherein $R_1$=cyclopropyl or cyclobutyl, which are very effective analgesics, at which no habituation and antagonistic morphine effects are assumed.

2. Description of the Prior Art

Compounds of a general formula (II) were prepared by means of a total synthesis (U.S. Pat. No. 3,819,635), or by means of a semisynthesis from a natural alkaloid thebaine (Mouralová, J. - Hájíček, J. - Trojánek, J.: Ceskoslov. Farm. 1 32, 23 (1983)).

4-phenoxy-14β-hydroxy-3-methoxymorphinan (III) is one of the intermediates of a semisynthesis:

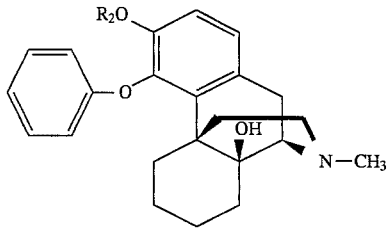

wherein $R_2$=$CH_3$, which is procurable after several synthesis steps from thebaine in a very good yield. Within the following step, a phenoxy-group is removed by means of a reduction with sodium in liquid ammonia, and an intermediate - 14β-hydroxy-3-methoxymorphinan (IV)

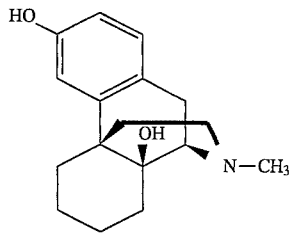

will be subjected to alkaline hydrolysis after the reaction with phenylchloroformate.

A key intermediate (-)-14β-hydroxy-3-methoxy-17-normorphinan (I) is reached on the basis of all the above-mentioned reactions, in which R=$CH_3$. Thus, the demanded compound (II) can be gained by means of several well-known procedures, i.e. either by means of a direct alkylation with cycloalkylmethylhalide, or by means of the O-demethylation (Czech patent appl. PV 163-93), or by means of acylation with cycloalkylcarbonylhalide followed by the reduction of carbonyl with complex hydrides and following O-demethylation (U.S. Pat. No. 3,819,635, Czech patent appl. PV 163-93). The O-demethylation can be ranked before alkylation or acylation, or among acylation and reduction of a carbonyl function.

SUMMARY OF THE INVENTION

Our works were aimed at finding the economic suitable methods of a synthesis of a semisynthetic morphinan alkaloid Butorphanol ((II), $R_1$=cyclobutyl), i.e. 3,14β-dihydroxy-17-cyclobutylmethyl-morphinan.

The newly proposed process, based on an intermediate of a semisynthesis of Butorphanol - 4-phenoxy-14β-hydroxy-3-methoxymorphinan (III), get-at-able from thebaine in a very good yield, do solve the preparation of two key intermediates ((I), R=H or $CH_3$) of synthesis of Butorphanol.

DISCLOSURE OF THE INVENTION

The main principle of this invention is the process for the preparation of 3,14β-dihydroxy-17-normorphinan having the formula (I):

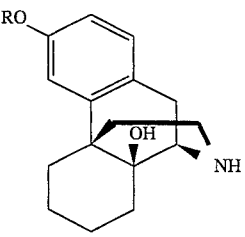

wherein R=hydrogen, comprising the reaction of the compound 4-phenoxy-14β-hydroxy-3-$R_2$oxymorphinan having the formula (III):

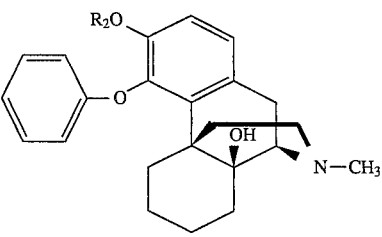

wherein $R_2$=hydrogen or methyl, with chloroformate having the formula (V):

$$R_3COOCl \quad (V)$$

wherein R=aryl, alkyl or halogenalkyl containing 2 to 4 carbon atoms in alkyl, with an advantage of phenyl, benzyl, ethyl, trichloroethyl, or 1-chloroethyl, to produce a mixture of intermediates having the formula (VI):

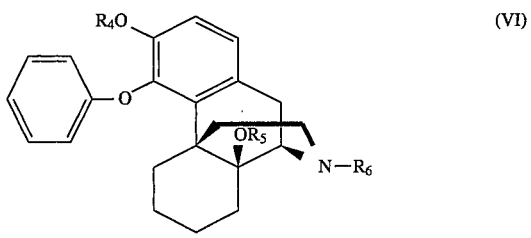

wherein $R_4$=hydrogen, methyl or $COOR_3$, $R_5$=hydrogen or $COOR_3$ and $R_6$=$COOR_3$, which without any further isolation will be subjected to a reaction with sodium in liquid ammonia to produce the compound corresponding to the formula (I), in which on the position R is hydrogen or methyl, and provided that R in formula (I) means methyl, the substance will be subjected to the O-demethylation with a complex of aluminium halide - dialkylsulfide to produce the compound having the formula compound (I), in which R means hydrogen.

To compare this above-mentioned procedure with known synthesis (Mouralová, J. - Hájíček, J. - Trojánek, J.: Ceskoslov. Farm. 1 32, 23 (1983)), a considerable simplification of an exacting semi-synthesis of Butorphanol from thebaine seems to be a great advantage by means of the number of reaction steps, which is reached by means of a suitable arrangement of the individual steps. In accordance with this procedure, the same effect can be reached at simultaneously increase of yield.

At the same time, both a phenoxy-group and a carbamate-group or a carbonate-group, being formed within a N-demethylation by means of chlorocarbonates, can be removed by means of a reduction with sodium in liquid ammonia. The O-demethylation can be carried-out with an advantage, e.g. by means of a complex of $AlCl_3$- $(CH_3)_2S$.

All the details of preparation method in accordance with the invention follow from the below-mentioned examples.

DETAILED DESCRIPTION OF THE PREFERRED EMBODIMENT

EXAMPLE 1

(-)-14β-hydroxy-3-methoxymorphinan ((I), R=$CH_3$)

26.6 ml (0,21 mol) of phenylchloroformate will be dropped during boiling, mixing and under the atmosphere of nitrogen for an hour to 10 g (26,4 mmol) of 4-phenoxy-14β-hydroxy-3-methoxymorphinan (III) solved in 150 ml of a dry 1,2-dichloroethane and at presence of 17,7 g (0,21 tool) of a dried and powdered $NaHCO_3$. A reaction mixture has been left under boiling for 16 hours. Then, $NaHCO_3$ was dissolved in water, an aqueous phase was separated, and an organic phase was concentrated to a honey evaporation residue formed with a mixture of intermediates (VII). This evaporation residue was dissolved in 40 ml of a dry tetrahydrofuran, and then it was added (dropped) into a liquid ammonia at the temperature of about –40° C. Small pieces of metallic sodium (11,0 g total amount) have been added into this mixture for eight hours. A reaction mixture was blue-coloured, and it meant that reaction has been finally finished.

Superfluous sodium was decomposed by means of addition of 11,0 g of ammonium chloride, and ammonium was evaporated by means of an increased temperature to the room temperature. Tetrahydrofuran was distilled-off, and evaporation residue (6,6 g) was crystallized from diethylether. 5,8 g (i.e. 80 %) of (-)-14β-hydroxy-3-methoxymorphinan in form of a white crystalline product were gained at a melting temperature of 109°–111° C. IR spectroscopy and NMR do correspond with a given structure.

EXAMPLE 2

(-)-3,14β-dihydroxymorphinan ((I), R=H)

Under cooling and mixing, 49 ml (0,67mol) of dimethylsulfide were added to 14,2 g (0,1 mol) of $AlCl_3$ in 145 ml of dichloromethane, and within one hour, a solution of 5,8 g (21,2 mmol) of 14β-hydroxy-3-methoxymorphinan in 145 ml of dichloromethane was added to this above-mentioned reaction mixture.

A reaction mixture has been mixed for one hour at the temperature of 25° C. Then, under cooling, a solution of 16,0 g (0,1 mol) of a tartaric acid in 150 ml of water was added, the organic layer was separated, and an aqueous layer was alkalized with 70 ml of $NH_4OH$ to pH 10, and extracted with chloroform.

Organic extracts were thickened to a foamy evaporation residue (4,7 g), and crystallized from methanol. 4,1 g (i.e. 75%) of (-)-3,14β-dihydroxymorphinan of a melting temperature of 263°–264° C. were gained.

IR spectroscopy and NMR do correspond with a given structure.

The mentioned invention can be utilized within pharmaceutical industry, i.e. in the production of a substance called BUTORPHANOL. This substance can be used as an effective analgesic, in the case of which no habituation and antagonistic morphine effects are assumed.

We claim:

1. Process for the preparation of 3,14β-dihydroxy-17-normorphinan having the formula (I)

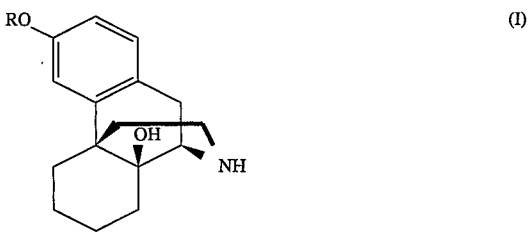

wherein R is hydrogen, comprising the reaction of the compound 4-phenoxy-14β-hydroxy-3-$R_2$oxymorphinan having the formula (III)

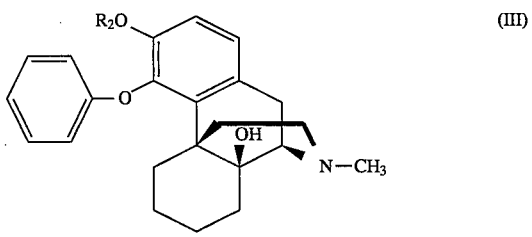

wherein $R_2$ is hydrogen or methyl, with chloroformate having the formula (V):

$$R_3COOCl \quad (V)$$

wherein $R_3$ represents aryl, alkyl or halogenalkyl containing 2 to 4 carbon atoms in alkyl, with an advantage of phenyl, benzyl, ethyl, trichloroethyl or 1-chloroethyl, to produce the mixture of intermediates having the formula (VI)

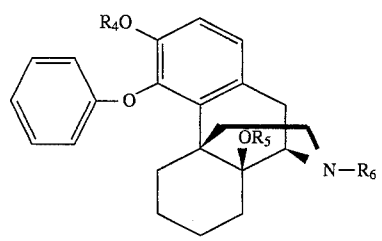
(VI)

wherein $R_4$ is hydrogen, methyl or $COOR_3$, $R_5$ is hydrogen or $COOR_3$, and $R_6$ is $COOR_3$, which will be subjected to a reaction with sodium in a liquid ammonia to produce the compound corresponding to formula (I), wherein on the position R is hydrogen or methyl, without any further isolation and provided that R in formula (I) means methyl, the substance will be subjected to the O-demethylation with a complex of aluminium halide - dialkylsulfide to produce the compound having the formula (I), in which R means hydrogen.

* * * * *